United States Patent
Sattler et al.

(10) Patent No.: US 7,564,949 B2
(45) Date of Patent: Jul. 21, 2009

(54) ANGIOGRAPHY DEVICE AND ASSOCIATED RECORDING METHOD WITH A MECHANISM FOR COLLISION AVOIDANCE

(75) Inventors: Stefan Sattler, Forchheim (DE); Reiner Staab, Baiersdorf (DE); Susanne Staab, legal representative, Baiersdorf (DE); Katharina Staab, legal representative, Aschaffenburg (DE); Silvia Rachor, legal representative, Goldbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/151,406

(22) Filed: May 6, 2008

(65) Prior Publication Data

US 2008/0279333 A1 Nov. 13, 2008

(30) Foreign Application Priority Data

May 9, 2007 (DE) .................. 10 2007 021 769

(51) Int. Cl.
*H05G 1/54* (2006.01)
(52) U.S. Cl. ..................... 378/117; 378/197
(58) Field of Classification Search .......... 378/62, 378/117, 193–198; 600/407
See application file for complete search history.

(56) References Cited

U.S. PATENT DOCUMENTS

| 7,302,040 | B2 * | 11/2007 | Camus ............... 378/117 |
| 7,379,533 | B2 * | 5/2008 | Koertge ............. 378/117 |
| 2005/0281374 | A1 | 12/2005 | Cheng et al. |
| 2006/0274888 | A1 | 12/2006 | Bernhardt et al. |
| 2007/0086570 | A1 | 4/2007 | Spahn |

FOREIGN PATENT DOCUMENTS

| DE | 10 2005 023 165 A1 | 11/2006 |
| DE | 10 2005 049 106 A1 | 4/2007 |

* cited by examiner

*Primary Examiner*—Courtney Thomas

(57) ABSTRACT

The present invention involves an angiography device for examining vessels of patients having an x-ray emitter and an associated detector, having an image processing unit, an image display unit, a control unit, a collision computer and sensors. The sensors, which are fastened to the angiography device, are designed to scan the outer dimensions of the patient prior to the actual examination and during the examination. The data obtained in this way can be fed into a memory of the collision computer and the system is controllable by a software of the collision computer such that the movement of the system when the system and patient become too close can be automatically slowed down or completely stopped by means of a the control unit.

19 Claims, 1 Drawing Sheet

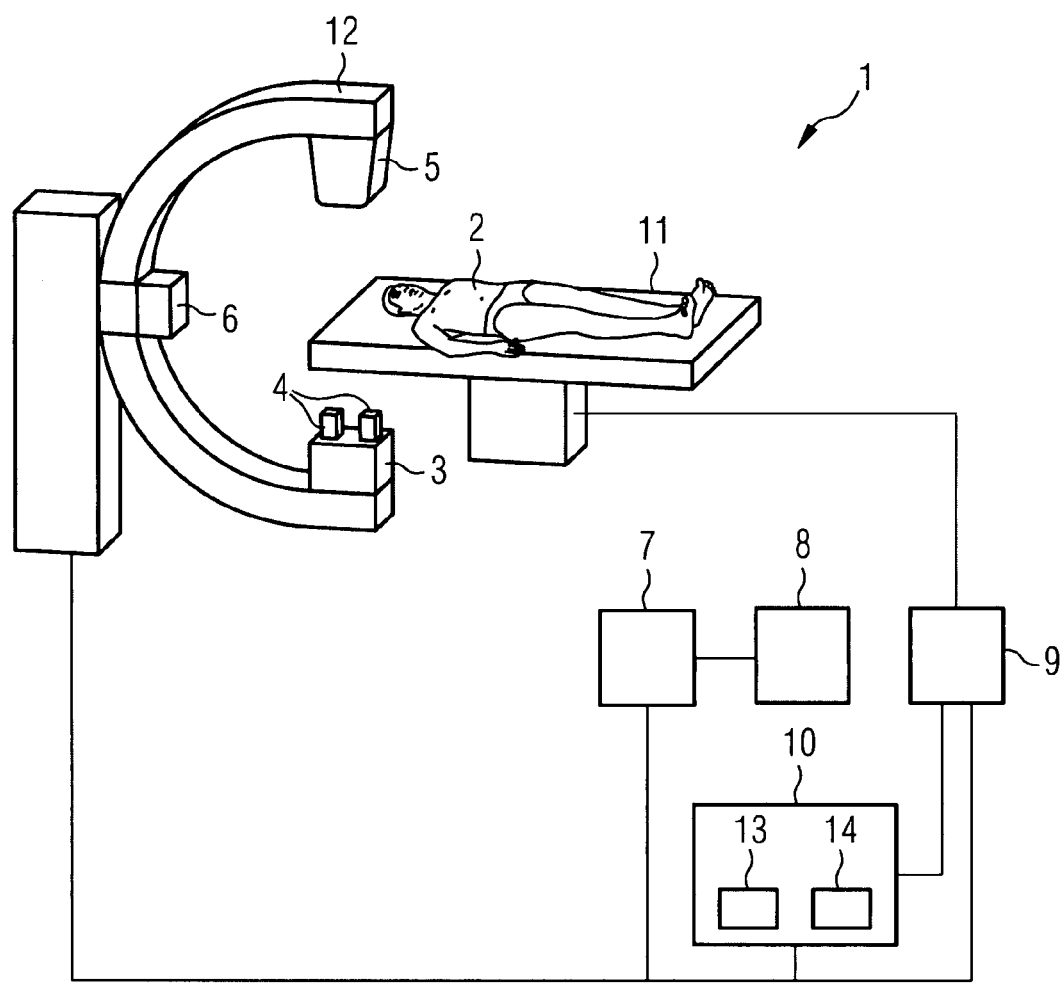

ANGIOGRAPHY DEVICE AND ASSOCIATED RECORDING METHOD WITH A MECHANISM FOR COLLISION AVOIDANCE

CROSS REFERENCE TO RELATED APPLICATIONS

This application claims priority of German application No. 10 2007 021 769.4 filed May 9, 2007, which is incorporated by reference herein in its entirety.

FIELD OF THE INVENTION

The present invention relates to an angiography device having an x-ray emitter, detector, image processing unit, image display unit, control unit, collision computer and sensors and an associated angiography method for the examination of the vessels of patients

BACKGROUND OF THE INVENTION

X-ray systems are nowadays to be assigned mostly in a dedicated fashion to a clinical application field. A distinction is thus made between angiography systems, fluoroscopy systems and radiography systems. In this classification, the two first-mentioned system groups can cover both dynamic applications as well as also single shots. Angiography, sonography, computer tomography, magnetic resonance tomography and optical coherence tomography are primarily available for the examination of blood vessels. The gold standard for the examination of vessels is angiography however. With interventions, i.e. if the examination achieves in making a narrowing of a vessel visible, in order to extend this and/or keep it open using a stent, there are currently no alternatives to angiography. Rotation angiography systems with a moveable C-arm are preferably used in order to record three-dimensional images of vessels.

Envelopes for the outer dimensions of a patient were previously assumed in order to avoid a collision between the moveable C-arm and the patient, said envelopes being disposed around the patient like a virtual balloon. The envelopes, which are stored in the collision computer of the angiography system, are assumed to be static and consist of several cylinders. In this way, provision can be made for instance for a cylinder for the head, a cylinder for the trunk, two for the arms and one for the legs. Irrespective of the actual size of the patient to be examined, only one static envelope exists, which has nothing to do with the specific silhouette of the patient. If the C-arm of the angiography system approaches the static envelope, the C-arm slows down. In order to protect patients of any body shape and size from colliding with the C-arm during the examination, the static envelope has to be dimensioned very large.

With the recordings according to the above prior art, a slow, manually controlled movement first takes place without x-rays, during which a collision computer is active, with it being monitored whether a collision of the C-arm with the table or with the static patient envelope, formed from the cylinders, occurs. A rapid imaging movement then takes place, during which the x-rays are applied. In this way, the collision computer is no longer active and the doctor is also no longer able to intervene. During the examination, the patient is assumed to be immobile.

US application US 2005/0281374 A1 discloses a prior art which claims a patient positioning system for a therapeutic radiation system with moveable components. The patient positioning system plans movements in advance and analyses these in order to increase the efficiency of the movement in the case of less latency time and to proactively avoid collisions. The patient positioning system contains a number of cameras, which can determine both the location of fixed and moveable system components as well as an infiltration of foreign objects or personal in the movement path. If a collision is impending, the system inhibits the movement of the patient positioning system. The fact that even the patient is also assumed to be immobile here is particularly characteristic of the aforementioned US application.

Electromechanical driving switches are used as a final means of stopping the system, before a patient is seriously injured by colliding with the C-arm. Such a switch can be integrated into the cladding of the C-arm for instance. The switches can be formed as limit switches, cut-off rubbers, tread mats etc.

The problem thus consists in the angiography system described in the prior art not being able to detect a movement of the patient during the examination using x-rays and thus not being able to get sufficiently close to the patient as a result of the large dimensioning of static envelopes of the C-arm at many points.

SUMMARY OF THE INVENTION

Based on the preceding, discussed disadvantages and problems, the invention addresses the object of further developing an angiography system such that unplanned and unintentional movements of the patient during his/her examination can be detected by the system in real-time, and in the event of a risk of the patient colliding with the C-arm, the movement of the C-arm or of the patient table stops immediately without the system first having to come to a stop, in a type of "emergency stop", by means of the electromechanical driving switch. To reduce the movement artifacts and shorten the examination times, higher speeds of the C-arm are needed in the future, as a result of which a dynamic mechanism for collision avoidance is necessary in order to protect the patient.

The present object is achieved by the features of the claims.

The present invention is advantageous for the following reason. Prior to the actual examination, the real outer dimensions of the patient are determined as the individual static envelope. During the actual examination, the real outer dimensions of the patient are determined in real-time as the dynamic envelope. The angiography device and in particular the C-arm or the patient table stops if the distance from individual static to dynamic envelopes exceeds an adjustable value for a position of the C-arm or patient table. This provides for a considerably improved protection of the patient from collisions with the C-arm of the angiography device, in comparison with the prior art, in the event of the patient moving beyond a certain threshold during the examination. In addition, the determination and use of individual static envelopes allows the C-arm to be moved very close to the patient during the actual examination.

BRIEF DESCRIPTION OF THE DRAWINGS

The invention is described in more detail below on the basis of the description of preferred exemplary embodiments, with reference to the drawing, in which;

FIGURE shows a schematic representation of an image of a C-arm angiography device having a C-arm, x-ray emitter, detector, image processing unit, image display unit, collision computer, control unit, patient table and an exemplary sensor.

DETAILED DESCRIPTION OF THE INVENTION

FIGURE shows an angiography device 1 according to the present invention. It involves an arrangement for examining vessels of patients 2 having an x-ray emitter 3 and an associated detector 5, an image processing unit 7, an image display unit 8, a control unit 9, a collision computer 10 and sensors 6, in which the sensors 6, which are attached to the angiography device 1, are designed to scan the outer dimensions of the patient 2 prior to the actual examination and during the examination and in which the data obtained in this way can be fed into a memory 14 of the collision computer 10 and the system can be controlled by a software 13 of the collision computer 10 such that the movement of the system can be automatically slowed down or completely stopped by the control unit 9 when the system and patient 2 are too close.

In order to increase the contrast, the vessels can be filled with a contrast agent during the examination. The contrast agent can be injected through a catheter directly to the site of the vascular system which is to be examined.

A first embodiment involves a system with a C-arm 12 and a patient table 11, with the emitter 3, diaphragm 4, detector 5 and sensors 6 being attached to the C-arm 12 and the C-arm 12 being rotatable or alternatively longitudinally moveable along the longitudinal axis of the patient table 11.

A second embodiment involves a system with a C-arm 12 and a patient table 11, with the emitter 3, diaphragm 4, detector 5 and sensors 6 being attached to the C-arm 12 and with the patient table 11 being longitudinally moveable along its longitudinal axis.

The above cited sensors 6 for the contactless distance measurement can be capacitive proximity sensors and/or ultrasound sensors and/or laser systems and/or camera systems and they can be attached to the C-arm 12 and/or the attachment components of the C-arm 12 such that the distance of the system from the patient 2 can be measured at every position of the C-arm 12 or of the patient table 11, and a patient envelope can be determined. The sensors 6 can be attached along the C-arm 12, preferably in the center of the C-arm 12 and/or on the detector 5 and/or on the diaphragm 4. The C-arm 12 can rotate about the isocenter and the rotational speed can amount here to 100 degrees per second or more.

The sensor data of the individual static patient envelope, which is determined prior to the actual examination, can be stored in the form of a look-up table in a memory 14 of the collision computer 10. Software 13 is also able to control the comparison of individual static patient envelopes with the dynamic patient envelopes recorded in real-time during the examination at each position of the movement path of the C-arm 12 or of the patient table 11.

Depending on the position of the C-arm 12 or of the patient table 11, i.e. depending on the measurement position, the adjustable tolerable deviation from dynamic to individual static envelopes can lie between 0.5 and 10 cm and beyond.

The invention also claims an angiography method for the x-ray examination of vessels of patients 2, in which an individual static patient envelope, which corresponds to the real patient silhouette, is first recorded during a slow movement of the C-arm 12 or of the patient table 11, which is manually controlled, and is forwarded to the collision computer 10 and in which a dynamic patient envelope, which is reconstructed from the data arriving permanently in real-time, is then generated during the actual x-ray examination while automatically moving the C-arm 12 or patient table 11, and in which, when the deviation of the dynamic from the individual static envelopes, determined by the collision computer 10, with a predetermined position of the C-arm 12 or of the patient table 11, exceeds a previously determined value, the movement of the C-arm 12 or of the patient table 11 is immediately slowed down or stopped by the central control unit 9.

During the determination of the dynamic patient envelope measured during the x-ray process, unwanted and unintentional movements of the patient 2 to be examined are thus detected by the sensors 6, which the associated data is recorded in the memory 14 and the data is evaluated by means of the software 13 of the collision computer 10.

In methods in which the C-arm 12 is moved, the system is designed such that the C-arm moves as quickly as possible during the actual x-ray examination.

One possible method is the rotation angiography. In this method, the C-arm 12 rotates about the patient table 11 and the patient 2 and a plurality of two-dimensional images of one and the same body region is recorded from different angles, with these images then being added together by the image processing unit 7 to form three-dimensional images of the examined body region.

A further method is the peripheral angiography method, with the C-arm 12 being stationary during the recording and the patient table 11 at the same time moving longitudinally along the longitudinal axis of the patient table 11, with two-dimensional images being recordable.

A further characteristic of the peripheral angiography method is a method according to which the C-arm 12 moves longitudinally along the longitudinal axis of the patient table 11 during the recording and the patient table 11 is stationary, with two-dimensional images being recordable.

The aforementioned methods involving recording an individual static envelope, which corresponds to the real patient silhouette, prior to the actual angiography record, compensating this envelope with the dynamic envelope measured in real-time during the angiography recording and evaluating the data in a collision computer, can be used universally to avoid a collision between the patient and angiography system. The method can be applied to any movement trajectories of the C-arm 12 and patient table 11, as well as to any combinations of movements of C-arm 12 and patient table 11.

The afore-described automatic and dynamic collision avoidance in consideration of the individual static patient envelope and unwanted movements of the patient 2 during the examination is all the more important the more quickly the C-arm 12 of an angiography system moves. To avoid movement artifacts and minimize the examination duration, rotation speeds of the C-arm 12 which exceed 100 degrees per second will be implemented in the future. As the high speed alongside the large bulk of the C-arm 12 generates an enormous pulse, the patient 2 can be severely injured in the event of a collision with the C-arm 12. A dynamic individual collision avoidance system is thus imperative, as described above.

The invention claimed is:

1. A medical device for examining a patient, comprising:
   a sensor that scans outer dimensions of the patient prior to the examination as a static patient envelope and the outer dimensions of the patient during the examination as a dynamic patient envelope;
   a collision computer that compares the static patient envelope with the dynamic patient envelope; and
   a control unit that controls a movement of a component of the medical device to avoid a collision between the component and the patient based on the comparison.

2. The medical device as claimed in claim 1, wherein the medical device is an angiography device comprising an x-ray emitter, a detector, a diaphragm, a C-arm, and a patient table.

3. The medical device as claimed in claim 2, wherein the component comprises the C-arm and the patient table.

4. The medical device as claimed in claim 2, wherein the sensor is attached to the C-arm, the detector, or the diaphragm.

5. The medical device as claimed in claim 2, wherein the C-arm rotates about an isocenter with a maximum speed of 100 degrees per second during the examination.

6. The medical device as claimed in claim 2, wherein the movement comprises a rotation or a longitudinal movement of the C-arm along a longitudinal axis of the patient table or a longitudinal movement of the patient table.

7. The medical device as claimed in claim 1, wherein the sensor is selected form the group consisting of: a capacitative proximity sensor, an ultrasound sensor, a laser sensor, and a camera.

8. The medical device as claimed in claim 1, wherein the static patient envelope is stored in the collision computer.

9. The medical device as claimed in claim 1, wherein a plurality of static patient envelopes are obtained by scanning the outer dimensions of the patient prior to the examination during a slow movement of the component at each position of a path of the movement of the component.

10. The medical device as claimed in claim 9, wherein the plurality of static patient envelopes are stored in the collision computer in a look-up table.

11. The medical device as claimed in claim 1, wherein the control unit automatically controls the movement of the component.

12. The medical device as claimed in claim 1, wherein the control unit slows down or stops the component if a result of the comparison exceeds a predetermined value.

13. The medical device as claimed in claim 12, wherein the predetermined value is between 0.5 cm and 10 cm depending on a position of the component.

14. A method for avoiding a collision of a component of a medical device with a patient being examined during an examination, comprising;
  obtaining a static patient envelope by scanning outer dimensions of the patient prior to the examination using;
  obtaining a dynamic patient envelope by scanning the outer dimensions of the patient during the examination;
  comparing the static patient envelope with the dynamic patient envelope; and
  avoiding the collision by controlling a movement of the component based on the comparison.

15. The method as claimed in claim 14, wherein a plurality of static patient envelopes are obtained by scanning the outer dimensions of the patient prior to the examination during a slow movement of the component at each position of a path of the movement of the component.

16. The method as claimed in claim 14, wherein a movement of the patient during the emanation is detected and evaluated along with the comparison.

17. The method as claimed in claim 14, wherein the medical device is an angiography device comprising an x-ray emitter, a detector, a diaphragm, a C-arm, and a patient table.

18. The method as claimed in claim 17, wherein the component comprises the C-arm and the patient table.

19. The method as claimed in claim 17, wherein the movement of the component comprises a rotation or a longitudinal movement of the C-arm along a longitudinal axis of the patient table or a longitudinal movement of the patient table.

* * * * *